(12) United States Patent
Simpson et al.

(10) Patent No.: US 11,129,970 B2
(45) Date of Patent: Sep. 28, 2021

(54) MECHANISMS FOR IMPROVING THE STIFFNESS TRANSITION ACROSS A DISSIMILAR METAL WELD JOINT

(71) Applicant: Abbott Cardiovascular Systems, Inc., Santa Clara, CA (US)

(72) Inventors: John A. Simpson, Carlsbad, CA (US); Bruce M. Wilson, Temecula, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 389 days.

(21) Appl. No.: 16/042,515

(22) Filed: Jul. 23, 2018

(65) Prior Publication Data

US 2018/0326187 A1 Nov. 15, 2018

Related U.S. Application Data

(62) Division of application No. 14/686,175, filed on Apr. 14, 2015, now Pat. No. 10,071,229.

(51) Int. Cl.
*A61M 25/09* (2006.01)

(52) U.S. Cl.
CPC ..... *A61M 25/09* (2013.01); *A61M 2025/0915* (2013.01); *A61M 2025/09091* (2013.01);
(Continued)

(58) Field of Classification Search
CPC .......... A61M 25/09; A61M 2025/0915; A61M 2025/09091; A61M 2025/09108; A61M 2025/09133
See application file for complete search history.

(56) References Cited

U.S. PATENT DOCUMENTS 4,951,677 A * 8/1990 Crowley .............. A61B 5/6848
600/109
5,165,421 A * 11/1992 Fleischhacker .... A61B 17/3207
138/130
(Continued)

FOREIGN PATENT DOCUMENTS

CN 104271035 1/2015
CN 104473626 4/2015
(Continued)

OTHER PUBLICATIONS

U.S. Appl. No. 14/686,175, filed Oct. 13, 2017, Office Action.
(Continued)

*Primary Examiner* — Rene T Towa
(74) *Attorney, Agent, or Firm* — Workman Nydegger; Randy Shen

(57) ABSTRACT

The present disclosure is directed to multi-segment intraluminal guide wires including an elongate distal portion comprising a first metallic material (e.g., nitinol), an elongate proximal portion comprising a second metallic material (e.g., stainless steel). The distal and proximal portions may be directly joined together end to end by a solid-state weld joint. A diameter of the weld region surrounding the weld joint on either side of the weld joint may be reduced (e.g., ground down) relative to the diameter of the distal and proximal portions of the guide wire on either side of the weld region. A stiffness adjusting sleeve may be disposed over the weld joint so that a transition profile of bending stiffness across the weld region is gradual, rather than abrupt across the distal portion of the guide wire to the proximal portion of the guide wire. A polymer jacket may cover the sleeve and distal portion.

19 Claims, 11 Drawing Sheets

(52) U.S. Cl.
CPC ............ *A61M 2025/09108* (2013.01); *A61M 2025/09133* (2013.01)

(56) References Cited

U.S. PATENT DOCUMENTS

| | | | |
|---|---|---|---|
| 6,001,068 | A | 12/1999 | Uchino et al. |
| 6,673,025 | B1 | 1/2004 | Richardson et al. |
| 6,866,642 | B2 | 3/2005 | Kellerman et al. |
| 6,918,882 | B2 | 7/2005 | Skujins et al. |
| 7,316,656 | B2 | 1/2008 | Shireman et al. |
| 7,455,646 | B2 | 11/2008 | Richardson et al. |
| 7,494,474 | B2 | 2/2009 | Richardson et al. |
| 7,722,551 | B2 | 5/2010 | Murayama et al. |
| 7,896,820 | B2 | 3/2011 | Satou et al. |
| 8,083,689 | B2 | 12/2011 | Vrba |
| 2004/0102720 | A1 | 5/2004 | Kellerman et al. |
| 2008/0200839 | A1* | 8/2008 | Bunch ................ A61M 25/09 600/585 |
| 2009/0221935 | A1* | 9/2009 | Murayama ............ B23K 31/02 600/585 |
| 2010/0174246 | A1 | 7/2010 | Bunch et al. |
| 2014/0200555 | A1 | 7/2014 | Simpson et al. |
| 2015/0005746 | A1* | 1/2015 | Sato ................ A61M 25/09 604/528 |
| 2015/0094616 | A1 | 4/2015 | Simpson et al. |
| 2015/0094690 | A1 | 4/2015 | Simpson et al. |
| 2016/0303353 | A1 | 10/2016 | Simpson et al. |

FOREIGN PATENT DOCUMENTS

| | | |
|---|---|---|
| EP | 0806220 | 11/1997 |
| JP | 2004230141 | 8/2004 |
| JP | 2005270466 | 10/2005 |
| JP | 2006296478 | 11/2006 |
| JP | 2008188670 | 8/2008 |
| WO | WO 03/030982 | 4/2003 |
| WO | WO 2016/167916 | 10/2016 |

OTHER PUBLICATIONS

U.S. Appl. No. 14/686,175, filed May 16, 2018, Notice of Allowance.

"Laser Spot Welding", Retrieved from https://www.amadaweldtech.eu/knowlegde-base/laser-spot-welding#:~:text=Laser%20spot%20welding%20is%20a,spot%20to%20weld%20metals%20together.&text=The%20light%20is%20absorbed%20by,melts%20some%20of%20the%20metal, accessed Mar. 19, 2021.

Dr. Kopeliovich, Dmitri, "Solid State Welding (SSW)", Retrieved from https://www.substech.com/dokuwiki/doku.php?id=solid_state_welding_ssw#:~:text=Solid%20State%20Welding%20is%20a,diffusion%20of%20their%20interface%20atoms, accessed Mar. 19, 2021.

What is Spot Welding? (A Complete Welding Process Guide), Retrieved from https://www.twi-global.com/technical-knowledge/faqs/what-is-spot-welding#:~:text=Spot%20welding%20(also%20known%20as,current%20to%20the%20weld%20area, accessed Mar. 19, 2021.

* cited by examiner

NO SLEEVE (assumes .0175" NiTi OD changes abruptly to .0165" SS OD at the weld interface)

| Position cm | Description | Core OD in | Core I in$^4$ | Core E lbs/in$^2$ | Core E·I lbs·in$^2$ | Sleeve ID in | Sleeve OD in | Sleeve I in$^4$ | Sleeve E lbs/in$^2$ | Sleeve E·I lbs·in$^2$ | Total E·I lbs·in$^2$ |
|---|---|---|---|---|---|---|---|---|---|---|---|
| 1 | Distal NiTi | 0.0175 | 4.60E-09 | 8.00.E+06 | 3.68E-02 | 0 | 0 | 0 | 0 | 0 | 3.683E-02 |
| 2 | Distal NiTi | 0.0175 | 4.60E-09 | 8.00.E+06 | 3.68E-02 | 0 | 0 | 0 | 0 | 0 | 3.683E-02 |
| 2 | Distal Sleeve | 0.0175 | 4.60E-09 | 8.00.E+06 | 3.68E-02 | 0 | 0 | 0 | 0 | 0 | 3.683E-02 |
| 3 | Weld distal | 0.0175 | 4.60E-09 | 8.00.E+06 | 3.68E-02 | 0 | 0 | 0 | 0 | 0 | 3.683E-02 |
| 3 | Weld proximal | 0.0165 | 3.64E-09 | 2.90.E+07 | 1.06E-01 | 0 | 0 | 0 | 0 | 0 | 1.055E-01 |
| 4 | Proximal Sleeve | 0.0165 | 3.64E-09 | 2.90.E+07 | 1.06E-01 | 0 | 0 | 0 | 0 | 0 | 1.055E-01 |
| 4 | Proximal SS | 0.0165 | 3.64E-09 | 2.90.E+07 | 1.06E-01 | 0 | 0 | 0 | 0 | 0 | 1.055E-01 |
| 5 | Proximal SS | 0.0165 | 3.64E-09 | 2.90.E+07 | 1.06E-01 | 0 | 0 | 0 | 0 | 0 | 1.055E-01 |

FIG. 10A

NITINOL SLEEVE (assumes both edges of the sleeve's pocket are square and butt directly against the end of the sleeve)

| Position cm | Description | Core OD in | Core I in$^4$ | Core E lbs/in$^2$ | Core E·I lbs·in$^2$ | Sleeve ID in | Sleeve OD in | Sleeve I in$^4$ | Sleeve E lbs/in$^2$ | Sleeve E·I lbs·in$^2$ | Total E·I lbs·in$^2$ |
|---|---|---|---|---|---|---|---|---|---|---|---|
| 1 | Distal NiTi | 0.0175 | 4.60E-09 | 8.00.E+06 | 3.68E-02 | 0 | 0 | 0 | 0 | 0 | 3.683E-02 |
| 2 | Distal NiTi | 0.0175 | 4.60E-09 | 8.00.E+06 | 3.68E-02 | 0 | 0 | 0 | 0 | 0 | 3.683E-02 |
| 2 | Distal Sleeve | 0.0145 | 2.17E-09 | 8.00.E+06 | 1.74E-02 | 0.0145 | 0.0175 | 2.43E-09 | 8.00.E+06 | 0.0194716 | 3.683E-02 |
| 3 | Weld distal | 0.0145 | 2.17E-09 | 8.00.E+06 | 1.74E-02 | 0.0145 | 0.0175 | 2.43E-09 | 8.00.E+06 | 0.0194716 | 3.683E-02 |
| 3 | Weld proximal | 0.0145 | 2.17E-09 | 2.90.E+07 | 6.29E-02 | 0.0145 | 0.0175 | 2.43E-09 | 8.00.E+06 | 0.0194716 | 8.240E-02 |
| 4 | Proximal Sleeve | 0.0145 | 2.17E-09 | 2.90.E+07 | 6.29E-02 | 0.0145 | 0.0175 | 2.43E-09 | 8.00.E+06 | 0.0194716 | 8.240E-02 |
| 4 | Proximal SS | 0.0165 | 3.64E-09 | 2.90.E+07 | 1.06E-01 | 0 | 0 | 0 | 0 | 0 | 1.055E-01 |
| 5 | Proximal SS | 0.0165 | 3.64E-09 | 2.90.E+07 | 1.06E-01 | 0 | 0 | 0 | 0 | 0 | 1.055E-01 |

FIG. 10B

STAINLESS STEEL SLEEVE (assumes both edges of the sleeve's pocket are square and butt directly against the end of the sleeve

| Position cm | Description | Core OD in | Core I in⁴ | Core E lbs/in² | Core E·I lbs·in² | Sleeve ID in | Sleeve OD in | Sleeve I in⁴ | Sleeve E lbs/in² | Sleeve E·I lbs·in² | Total E·I lbs·in² |
|---|---|---|---|---|---|---|---|---|---|---|---|
| 1 | Distal NiTi | 0.0175 | 4.60E-09 | 8.00.E+06 | 3.68E-02 | 0 | 0 | 0 | 0 | 0 | 3.683E-02 |
| 2 | Distal NiTi | 0.0175 | 4.60E-09 | 8.00.E+06 | 3.68E-02 | 0 | 0 | 0 | 0 | 0 | 3.683E-02 |
| 2 | Distal Sleeve | 0.0145 | 2.17E-09 | 8.00.E+06 | 1.74E-02 | 0.0145 | 0.0175 | 2.43E-09 | 2.90.E+07 | 0.0705845 | 8.794E-02 |
| 3 | Weld distal | 0.0145 | 2.17E-09 | 8.00.E+06 | 1.74E-02 | 0.0145 | 0.0175 | 2.43E-09 | 2.90.E+07 | 0.0705845 | 8.794E-02 |
| 3 | Weld proximal | 0.0145 | 2.17E-09 | 2.90.E+07 | 6.29E-02 | 0.0145 | 0.0175 | 2.43E-09 | 2.90.E+07 | 0.0705845 | 1.335E-01 |
| 4 | Proximal Sleeve | 0.0145 | 2.17E-09 | 2.90.E+07 | 6.29E-02 | 0.0145 | 0.0175 | 2.43E-09 | 2.90.E+07 | 0.0705845 | 1.335E-01 |
| 4 | Proximal SS | 0.0165 | 3.64E-09 | 2.90.E+07 | 1.06E-01 | 0 | 0 | 0 | 0 | 0 | 1.055E-01 |
| 5 | Proximal SS | 0.0165 | 3.64E-09 | 2.90.E+07 | 1.06E-01 | 0 | 0 | 0 | 0 | 0 | 1.055E-01 |

FIG. 10C

MECHANISMS FOR IMPROVING THE STIFFNESS TRANSITION ACROSS A DISSIMILAR METAL WELD JOINT

CROSS-REFERENCE TO RELATED APPLICATIONS

This application is a divisional of U.S. patent application Ser. No. 14/686,175, filed Apr. 14, 2015, now U.S. Pat. No. 10,071,229, the entire contents of which are incorporated by reference herein.

BACKGROUND

The human body includes various lumens, such as blood vessels or other passageways. A lumen may sometimes become at least partially blocked or weakened. For example, a lumen may be at least partially blocked by a tumor, by plaque, or both. An at least partially blocked lumen may be reopened or reinforced with an implantable stent.

A stent is typically a tubular body that is placed in a lumen of the body. A stent may be delivered inside the body by a catheter that supports the stent in a reduced-size configuration as the stent is delivered to a desired deployment site within the body. At the deployment site, the stent may be expanded so that, for example, the stent contacts the walls of the lumen to expand the lumen.

A guide wire may be employed when delivering a delivery catheter and stent to a desired location. For example, a guide wire may be advanced through a guiding catheter until the distal tip of the guide wire extends just beyond the location where the stent is to be implanted. A catheter and a stent to be positioned may be mounted onto the proximal portion of the guide wire, and the catheter and stent may be advanced over the guide wire until the catheter and stent are disposed within the blood vessel or other passageway where the stent is to be implanted. Once the stent is implanted, the catheter may be withdrawn over the guide wire. The guide wire may also be withdrawn, and the stent typically left in place.

Guide wires may often include an elongate core member with one or more segments near the distal end that taper distally to smaller cross-sections. One major requirement for guide wires is that they provide sufficient column strength to be pushed through the patient's vasculature or other body lumen without buckling. On the other hand, they must be sufficiently flexible to avoid damaging the body lumen as they are advanced. Efforts have been made to improve both strength and flexibility of guide wires to make them more suitable for these purposes, although these two desired characteristics are generally diametrically opposed to one another, such that an improvement in one typically results in less satisfactory performance relative to the other. For example, it is desirable that the distal portion of the guide wire be relatively more flexible in order to be more easily navigable through the patient's vasculature, which may be quite tortuous in portions. The proximal portion may be increasingly stiff, to provide the ability to support a balloon catheter or similar device.

Despite a number of different approaches for addressing these issues, there still remains a need for improved guide wires and associated methods of manufacture.

SUMMARY

For instance, in one configuration, the present disclosure is directed to a multi-segment intravascular guide wire including an elongate distal core wire portion (e.g., a first portion) comprising a first metallic material, and an elongate proximal core wire portion (e.g., a second portion) comprising a second, different metallic material. The distal and proximal portions may be directly joined together end-to-end (e.g., by a solid-state weld joint). Such a weld joint may be surrounded by a weld region, which weld region is reduced in diameter relative to the diameters of the distal and proximal portions of the guide wire on either side of the weld region. The guide wire may include a stiffness adjusting sleeve disposed over the weld joint (e.g., covering the reduced diameter across the weld region). The stiffness adjusting sleeve results in a bending stiffness transition profile across the weld region that is gradual, rather than abrupt. The stiffness adjusting sleeve may be formed from a multifilar coil including multiple strands of helically wound wire, and/or may include a sleeve body in which at least one end thereof is tapered in thickness.

Another embodiment of the present disclosure is directed to a method for forming a multi-segment intravascular guide wire. Such a method may include providing initially separate distal and proximal guide wire segments, which segments comprise different metallic materials (e.g., nitinol and stainless steel, respectively). The distal and proximal segments are aligned with one another, end-to-end, and may be solid-state welded directly to one another at a weld joint. The diameter at the weld region surrounding the weld joint is reduced (e.g., machined away) so that the diameter of the weld region is less than the diameter of the adjacent distal and proximal segments on either side of the weld region. A hollow cylindrical stiffness adjusting sleeve is positioned over the weld region (e.g., within a "pocket" or "trough" corresponding to the reduced diameter). In an embodiment, the stiffness adjusting sleeve may be a multifilar coil including multiple strands of helically wound wire disposed over the weld region, and/or may comprise a sleeve body in which at least one end thereof is tapered in thickness. In either case, the stiffness adjusting sleeve results in a bending stiffness transition profile across the weld region that is gradual, rather than abrupt.

According to an embodiment of the present disclosure, the multi-segment intravascular guide wire including an elongate distal core wire portion comprising a first metallic material, and an elongate proximal core wire portion comprising a second, different metallic material, joined together end-to-end, with includes a stiffness adjusting sleeve disposed over the weld region surrounding the weld joint may be such that the weld joint is disposed in relative close proximity relative to the distal end or tip of the guide wire. For example, the weld joint may be no more than 25 cm, no more than 20 cm, no more than 15 cm, or no more than 10 cm (e.g., 3 cm, 6 cm, etc.) from the distal end of the guide wire.

In an embodiment, a polymer jacket may be provided over at least the stiffness adjusting sleeve disposed over the weld joint. The polymer jacket may also cover the distal end of the guide wire. In an embodiment, the abutting proximal and distal core wire portions may be provided with different diameters at the abutting weld joint (e.g., with the more flexible distal core wire portion being relatively larger in diameter), so as to at least partially compensate for the significantly lower Young's modulus of the metallic material from which the distal core wire portion is formed. A polymer jacket may aid in smoothing over, and/or filling in any gaps resulting from such differences in outside diameter of the metallic core wire portions, tapering of one or both ends of the stiffness adjusting sleeve, etc., so as to provide a smooth exterior profile over region surrounding the weld joint and sleeve. If desired, a constant outside diameter may be provided as a result of the polymer jacket (i.e., the jacket may vary in thickness, filling any gaps, etc.).

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify at least some of the advantages and features of the present disclosure, a more particular description of the disclosure will be rendered by reference to various embodiments thereof that are illustrated in the appended drawings. It is appreciated that these drawings depict only various embodiments of the disclosure and are therefore not to be considered limiting of its scope. The various embodiments will be described and explained with additional specificity and detail through the use of the accompanying drawings in which:

FIGS. 10A-10C include tables showing characteristics of the sleeves and guide wire segments of the configurations corresponding to FIGS. 9A-9C.

DETAILED DESCRIPTION

I. Introduction

Figure 1:
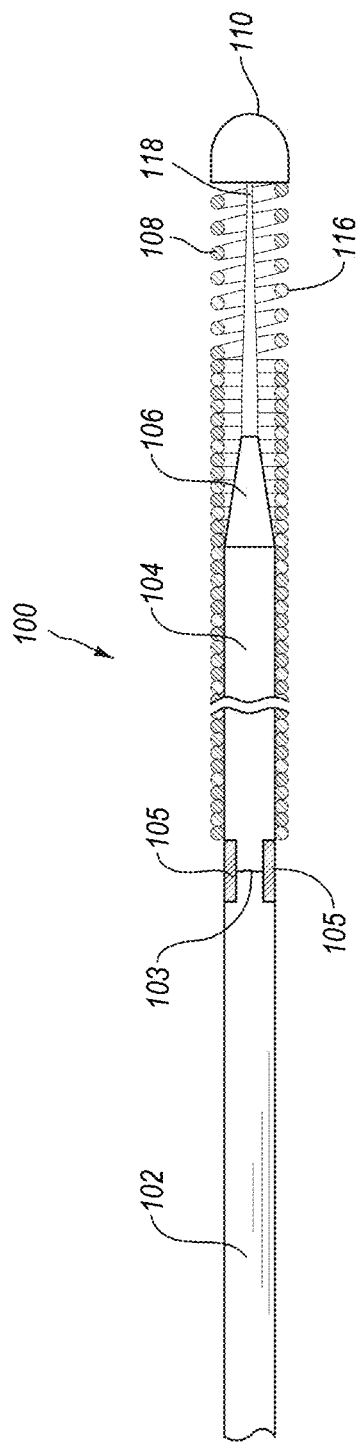
FIG. 1 is a side elevation and partial cross-sectional view of a multi-segment intraluminal guide wire according to an embodiment of the present disclosure.

In an embodiment, the present disclosure is directed to multi-segment intraluminal guide wires including an elongate first distal portion comprising a first metallic material (e.g., nitinol), an elongate second proximal portion comprising a second metallic material (e.g., stainless steel) that is different from the first metallic material. The distal and proximal elongate portions may be directly joined together end-to-end by a solid-state weld joint. A diameter of the weld region surrounding the weld joint on either side of the weld joint may be reduced (e.g., ground down) relative to the diameter of the distal and proximal portions of the guide wire on either side of the weld joint. A stiffness adjusting sleeve may be disposed over the weld joint so that a transition profile of bending stiffness across the weld region is more gradual, rather than abrupt across the distal portion of the guide wire to the proximal portion of the guide wire. In an embodiment, the stiffness adjusting sleeve may be formed from a multifilar coil including multiple strands of helically wound wire disposed over the weld region so that a transition profile of bending stiffness across the weld region is gradual rather than abrupt. The weld joint may be relatively close to the distal end of the distal portion of the guide wire (e.g., within 25 cm of the end, within 20 cm, 15, cm or 10 cm of the end). A polymer jacket may be disposed over at least the stiffness adjusting sleeve, e.g., and at least over a portion of the distal portion of the guide wire. In an embodiment, the stiffness adjusting sleeve may include a sleeve body in which at least one end thereof (e.g., the proximal end disposed over a stainless steel proximal guide wire portion) is tapered in thickness, which tapering further aids in providing a transition profile of bending stiffness across the weld region that is more gradual, rather than abrupt.

Another embodiment of the present disclosure is directed to a method for forming a multi-segment intraluminal guide wire including providing initially separate distal and proximal guide wire segments, which segments comprise different metallic materials (e.g., nitinol and stainless steel), aligning the separate segments end-to-end, and welding (e.g., solid-state welding) the separate distal and proximal segments to one another at a weld joint (e.g., directly welded to one another). The diameter of the weld region surrounding the weld joint may be reduced, relative to the distal and proximal segments of the guide wire on either side of the weld region. A stiffness adjusting sleeve may be positioned over the weld region. The sleeve may be reduced radially (e.g., through rotary swaging, crimping, etc.) so that it is seated within the reduced diameter section over the weld joint. The weld joint may be relatively close to the distal end of the distal portion of the guide wire (e.g., within 25 cm of the end, within 20 cm, 15, cm or 10 cm of the end). A polymer jacket may be applied over at least the stiffness adjusting sleeve, e.g., and at least a portion of the distal portion of the guide wire. In an embodiment, the sleeve may be formed from a multifilar coil, and/or may comprise a sleeve body in which at least one end thereof (e.g., the proximal end) is tapered in thickness. The sleeve serves to alter the transition profile of bending stiffness across the weld region from being abrupt (as would occur due to the weld joint alone) to more gradual.

II. Exemplary Multi-Segment Intraluminal Guide Wires

It is beneficial to provide a multi-segment intraluminal guide wire including a proximal segment or portion formed of a metallic material having greater Young's modulus (i.e., greater stiffness), and a distal segment or portion formed of a metallic material having lower Young's modulus than the proximal segment. The terms segment and portion may be used interchangeably herein. By way of example, such a proximal portion may be formed from stainless steel, and the distal portion formed of nitinol. This provides the distal end of the guide wire with great flexibility and durability, while giving the proximal end great support and torque transmission. However, when butt welding the distal and proximal segments to one another, particularly where the weld joint extends generally perpendicular to the longitudinal axis of the guide wire, the weld region exhibits an abrupt stiffness transition at the weld joint because the Young's modulus for nitinol, either in superelastic or linear elastic form, is substantially lower than that of stainless steels (e.g., AISI 304 or 316) or cobalt-based alloys (e.g., L605 or MP35N). For example, this difference is approximately two to four-fold, as Young's modulus for nitinol is about 8-10 Msi versus about 20-35 Msi for austenitic stainless steels and cobalt-based alloys, depending upon the degree of anisotropy due to crystallographic texture within the latter.

In guide wire configurations where for maximum torque transmission or other reasons, it is desirable for the weld joint to be located relatively close to the distal end of the guide wire (e.g., within 25 cm of the end), the abrupt change in Young's modulus associated with the weld joint may adversely impact the ability of the guide wire to advance through tortuous vasculature. The presently disclosed embodiments reduce the abruptness of the change in stiffness across the weld joint by altering the transition profile of bending stiffness so as to be more gradual, rather than abrupt, even while the weld joint itself may be generally perpendicular relative to the longitudinal axis of the guide wire.

FIG. 1 is an elevation side view and partial cross-section view of a guide wire 100 including features according to the present disclosure. Guide wire 100 may be adapted for insertion into a body lumen of a patient, for example a vein or artery. Guide wire 100 may include an elongate, relatively high strength proximal core portion 102 that may be directly welded to a relatively flexible distal core portion 104 at weld joint 103. Over weld joint 103 is provided a stiffness adjusting sleeve 105, which aids in making the transition profile of bending stiffness across weld region 103 more gradual, rather than abrupt and focused entirely at weld joint 103, as may occur where weld joint 103 is generally perpendicular to a longitudinal axis of the guide wire 100, as shown. Stiffness adjusting sleeve 105 includes and contributes significant stiffness, so that when attached over the weld region it increases and contributes to stiffness on each side of the weld joint as compared to its absence. It is not merely a reinforcing sleeve which adds no significant stiffness, as in U.S. Pat. No. 6,866,642. For example, stiffness adjusting sleeve 105 may be metallic (e.g., nitinol—the same material as the distal core portion), with sufficient thickness to affect stiffness across the weld region (e.g., it may typically be about 0.001 to 0.004, or 0.002 to 0.003 inch in wall thickness).

As seen in FIG. 1, the diameter in the weld region (the weld joint and surrounding area) is reduced in diameter during fabrication to accommodate insertion of the sleeve 105 therein. Stiffness adjusting sleeve 105 will be discussed in greater detail below. Distal core portion 104 may include a tapered section 106, tapering to a smaller thickness in the distal direction. A helical coil 108 may be disposed about distal core section 104, which may be secured to rounded tip 110. Although weld joint 103 is shown as being at a location proximal to the helical coil 108 and tapered section 106, and a tapered section between 106 and 118, it will be appreciated that in some embodiments, particularly where the weld joint is very close to distal end 110 (e.g., within 15 cm, within 10 cm, within 6 cm, or within 3 cm of the end), the weld joint 103 may not necessarily be distal to these features (e.g., it could be covered by coil 108, it could be on a tapered portion, or distal to a tapered portion).

A distal section 116 of coil 108 may be stretched in length to provide additional flexibility, with gaps, or larger gaps between adjacent coils 108. Distal tip 118 of distal core portion 104 may be secured to rounded tip 110 to prevent passage of distal tip 118 through any spaces between any stretched coils 108. At least a portion of distal tip 118 of core portion 104 may be cold worked or otherwise configured to reduce resiliency in the extreme distal portion of tip 118 (e.g., so as to more readily accept a J, L, or other bend). This may be done by flattening the desired extreme distal portion of tip 118 (e.g., to a rectangular cross-section), or by otherwise imparting cold work. In some embodiments, the extreme distal portion of tip 118 may be circular in transverse cross-section, even after such cold work or other treatment. Guide wire core tips featuring such circular cross-sections after having been cold worked are disclosed in U.S. patent application Ser. Nos. 14/042,321 and 14/499,856, herein incorporated by reference in their entirety.

Figure 2:
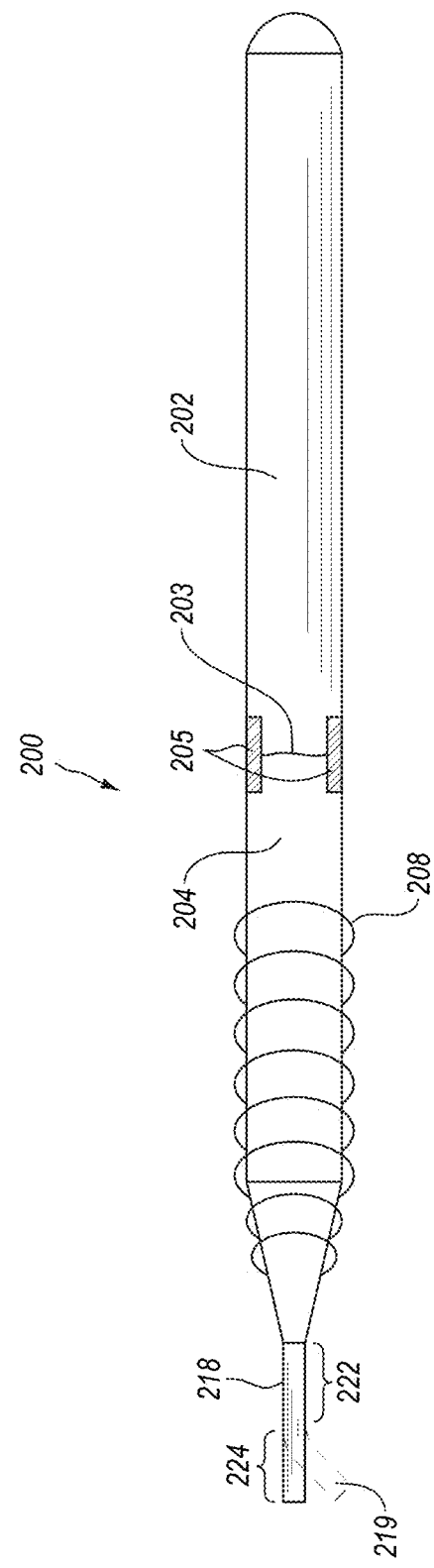
FIG. 2 is a simplified side elevation view of a multi-segment intraluminal guide wire according to an embodiment of the present disclosure.

FIG. 2 shows a simplified embodiment of another intraluminal guide wire 200 including features of the present disclosure. Core portions 202 and 204 may be directly welded together at weld joint 203 during fabrication. Portion 202 may comprise a material (e.g., stainless steel) having a relatively higher modulus of elasticity. A distal end of portion 202 may be directly joined through a weld (e.g., a solid-state end-to-end butt weld) to distal portion 204, which comprises a different material (e.g., nitinol), having a relatively lower modulus of elasticity. Distal portion 204 may include a shapable distal tip 218 which can be permanently deformed (e.g., by finger pressure) to create a tip that can be steered through a patient's vasculature, similar to tip 118. As shown, distal tip 218 may be bent or deformed into a J, L or similar bend 219. A coil 208 may be disposed over a portion of distal core portion 204. As with embodiment 100, although weld joint 203 and sleeve 205 is shown as being proximal to various features (coil 208, a tapered distal portion a, etc., it will be appreciated that the weld joint may be more distally disposed than illustrated).

Figure 3:
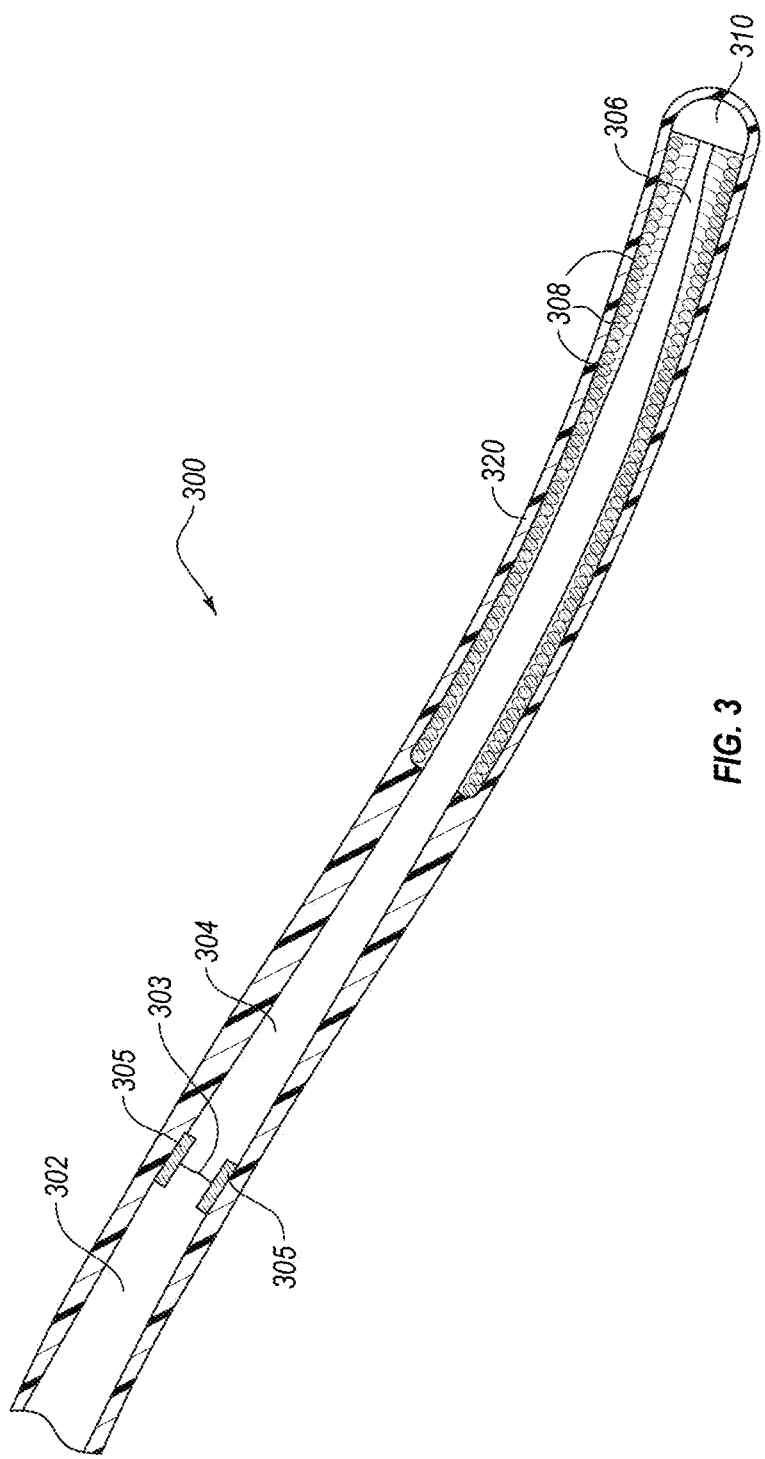
FIG. 3 is a side elevation and partial cross-sectional view of a multi-segment intravascular guide wire including a polymer jacket according to an embodiment of the present disclosure.

FIG. 3 shows another embodiment of an intraluminal guide wire 300 including features of the present disclosure. Guide wire 300 may include a proximal core portion (e.g., stainless steel, a cobalt-based alloy, etc.) 302 and a distal core portion 304 that may be directly welded together at joint 303. Distal core wire portion 304 may be tapered at 306, as tip 318 approaches rounded tip 310. Coils 308 may be disposed over distal core portion 304. Coils 308 may extend proximally to any degree desired. In an embodiment, coils 308 may extend over weld joint 303, part or all of stiffness adjusting sleeve 305, and/or even a part of proximal core portion 302, particularly where weld joint 303 is relatively close to the distal tip of the guide wire (e.g., within 25 cm, within 20 cm, within 15 cm, within 10 cm, etc.). Guide wire 300 is shown as including a polymer jacket 320 that covers at least the distal end of guide wire 300 (e.g., rounded tip 310, coils 308, and distal core wire portion 304). As shown, polymer jacket 320 may cover weld region 303, and all or at least a portion of sleeve 305.

In any of embodiments 100, 200, and 300, the respective weld joint may typically include a heat affected zone surrounding the weld joint (103, 203, or 303) as a result of solid state deformation of the materials within this region. The length of the reduced portion into which the respective sleeve (105, 205, 305) is seated may be at least equal to that of the heat affected zone. Typically, the length of the sleeve may be greater than that of the heat affected zone. For example, a typical length of the stiffness adjusting sleeve may be 0.5 cm to 4 cm, 1 cm to 3 cm, or about 2 cm.

The illustrated configurations for guide wires 100, 200, and 300 are merely three of many possible configurations, and other guide wire configurations including multiple segments that may be welded or otherwise joined together, and where a stiffness adjusting sleeve is provided over the weld joint are encompassed by the present disclosure.

The distal core section (e.g., 104, 204, 304) may be made of a nickel-titanium alloy such as nitinol, a superelastic alloy including about 30 atomic percent to about 52 atomic percent titanium, with the balance typically being nickel. Optionally, up to about 10 atomic percent or up to about 3 atomic percent of one or more other alloying elements may be included. Other alloying elements include, but are not limited to iron, cobalt, chromium, vanadium, platinum, palladium, copper, and combinations thereof. Where platinum, palladium, copper, vanadium, or combinations thereof are included, each may be included in amounts of up to about 10 atomic percent in one embodiment. In one embodiment, where iron, cobalt, chromium, or combinations thereof are included, each may be included in amounts of up to about 3 atomic percent.

Addition of nickel above equiatomic amounts relative to titanium increases stress levels at which the stress induced austenite to martensite transition occurs. This characteristic can be used to ensure that the temperature at which the martensitic phase thermally transforms to the austenitic phase is well below human body temperature (37° C.) so that the austenite is the only temperature-stable phase at body temperature. Excess nickel may also provide an expanded strain range at very high stresses when the stress induced transition occurs during use, which has the tactile benefit of raising its apparent stiffness.

Because of the extended strain range characteristics of nitinol, a guide wire having a distal portion made at least in substantial part of such material can be readily advanced through tortuous arterial passageways with minimal risk of kinking. Such characteristics are similarly beneficial where the distal nitinol portion of the guide wire may be prolapsed, either deliberately or inadvertently. If desired, such nitinol alloys may be treated to result in linear elastic properties, exhibiting increased apparent stiffness as compared to the superelastic form, due to the absence of the characteristic stress plateaus caused by the reversible austenite/martensite transformations responsible for superelasticity. Other materials including similar properties (e.g., other superelastic or otherwise highly resilient alloys) may similarly be employed, nitinol merely being an example.

The proximal portion (e.g., 102, 202, 302) of the guide wire may typically be significantly stronger (i.e., having higher yield and tensile strengths) than the distal portion. For example, the proximal portion may be formed of stainless steel (e.g., SAE 304 stainless steel). Other high strength materials, including, but not limited to cobalt-based alloys such as MP35N and/or L605 may also be employed.

Applicant has found it can be incredibly difficult to consistently weld incompatible, dissimilar materials (such as stainless steel and nitinol) directly to one another. For example, even if a weld connection can be made, localized variability at the dissimilar material interface or within the surrounding heat affected zone can result in weld integrity that may be diminished seemingly at random, with no known nondestructive method of detection. As a result, many such proposed or even existing dissimilar welded components can exhibit undesirably high variations in weld performance, with unpredictable failure characteristics.

Because of these difficulties in directly welding such dissimilar materials together, often such direct weld connections have been avoided by indirectly joining the stainless steel (for example) and nitinol (for example) segments to one another by employing a third transition piece positioned between the incompatible materials (e.g., see U.S. Pat. No. 7,316,656), or by joining them without resorting to a weld (e.g., use of an adhesive and/or a coupling). Applicant has found that direct welding of such dissimilar materials can be achieved, as described in U.S. Publication No. 2014/0200555, herein incorporated by reference in its entirety. While direct welding of the dissimilar metallic materials alone may be preferred, it will be appreciated that a stiffness adjusting sleeve as described herein may also be employed in alternative constructions.

Figure 4:
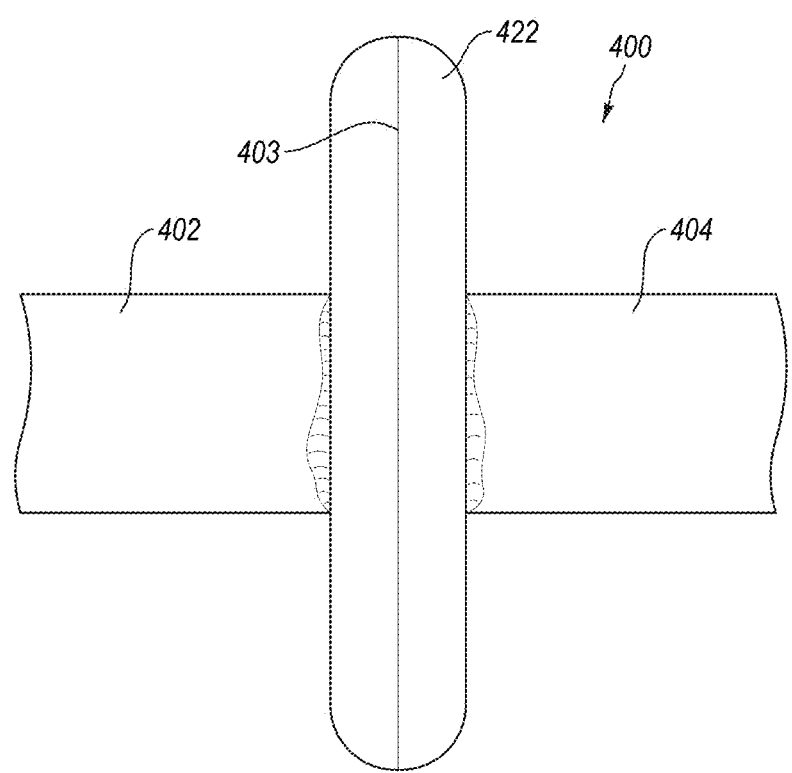
FIG. 4 is a close up side elevation view showing the weld region and the weld nugget formed when directly joining the two segments of the guide wire together by solid-state welding.

FIG. 4 shows welding attachment of such two dissimilar core wire portions 402 and 404. Such may be achieved through a solid-state resistance welding process in which the abutting portions of the segments undergo controlled heating and deformation without melting of either material, as melting can result in poor weld ductility and other problems (e.g., formation of undesirable intermetallic compounds, etc.). A metallurgical bond is created while both materials remain in the solid state, typically through simultaneous application of heat and pressure at the interface of the dissimilar metals.

Briefly described, the separate portions or segments (e.g., 402 and 404) of the core wire 400 are aligned (e.g., axially, end-to-end) with one another. Axial force is applied while delivering electrical current through the guide wire portions 402 and 404. A weld nugget 422 forms between the guide wire portions or segments, as a result of the applied pressure and heat. The thickness of the weld nugget 422 may represent the thickness of heat affected zone (or at least the majority of the heat affected zone) surrounding the weld joint 403. For example, the heat affected zone may typically have a thickness of less than about 0.25 mm, less than about 0.20 mm, less than about 0.18 mm, or from about 0.15 mm to about 0.18 mm. In an example, the weld nugget may have an average thickness of about 0.15 mm. The core wire segments 402 and 404 may typically be relatively thin. For example, in an embodiment, they may have a diameter from about 0.013 inch to about 0.020 inch (e.g., nominally 0.014 or 0.018 inch).

In an embodiment, the diameters of the two may be substantially identical to one another. In another embodiment, one of the core wire portions may intentionally be narrower than the other. For example, the distal core wire portion may be intentionally sized to be larger than the proximal core wire portion. Such an embodiment may further aid to reduce the difference in bending stiffness between the two portions, as bending stiffness of cylindrical members is proportional to diameter to the $4^{th}$ power. For example, as such, a slightly larger diameter provided to the lower Young's modulus distal core wire portion may greatly aid in reducing any difference in bending stiffness between the two portions. For example, in an embodiment, the end of the distal core wire portion that is welded end-to-end relative to the end of the proximal core wire portion may be 2% to 15%, 3% to 10%, or 4% to 8% larger in diameter than the interfacing end of the proximal core wire portion. The specific amount selected may depend on the actual difference in Young's modulus between the two materials, as well as other factors. By way of example, in an embodiment, for a nominal 0.018 inch guide wire, a stainless steel proximal core wire portion having a weld end diameter of 0.0165 inch and a nitinol distal core wire portion having a weld end diameter of 0.0175 inch may be employed. During manufacture, the weld region, and the entire nitinol length may be ground to below 0.0165 inch after welding. The weld region may be ground to about 0.0145 inch or smaller, where a polymer jacket is to be applied over the weld. A polymer jacket applied after welding may smooth over any remaining differences, providing a constant exterior diameter (or a desired smooth taper) over the weld joint transition, and distal core wire portion.

As shown in the Figures, in an embodiment, the weld joint 403 may be substantially perpendicular relative to the longitudinal axis A of the resulting guide wire. Such a perpendicular arrangement is easier to work with when pressing the two core wire portions together, whereas a ramped interface between the two segments results in the two core portions having a tendency to slide over and past one another when applying pressure, rather than maintaining the two core portions in a desired alignment.

While a ramped configuration may be desirable in theory as aiding in reducing the abruptness of a transition profile of bending stiffness across the joint (e.g., see U.S. Pat. Nos. 6,866,642 and 6,001,068), it can be incredibly difficult to achieve a reliable solid state weld between the two segments as a practical matter, particularly when considering that the core wire portions are so small in diameter (e.g., 0.013 inch to 0.020 inch) to begin with. Such tapered or ramped ends as shown in FIG. 17 of U.S. Pat. No. 6,001,068 or FIGS. 1 and 2 of U.S. Pat. No. 6,866,642 in effect become knife edges, and tend to slide past one another during attempted alignment, particularly where welding involves continued application of axial force. In addition to the difficulty in preventing sliding of such interfacing surfaces past one another, such structures can present a safety hazard as well. For at least these reasons, in at least some embodiments, it is preferred that the weld joint (and the ends of the core wire portions 402 and 404 before their attachment to one another) be substantially perpendicular to the longitudinal axis of the guide wire 400. Although a perpendicular orientation of 90° may be preferred, suitable results may still be obtained (e.g., preventing slippage between initially separate segments being pressed together during welding) with nearly perpendicular angles. For example, any angle between the weld joint and the longitudinal axis of the guide wire may be within 1°, within 3°, within 5°, or within 10° of perpendicular.

Figure 5A:
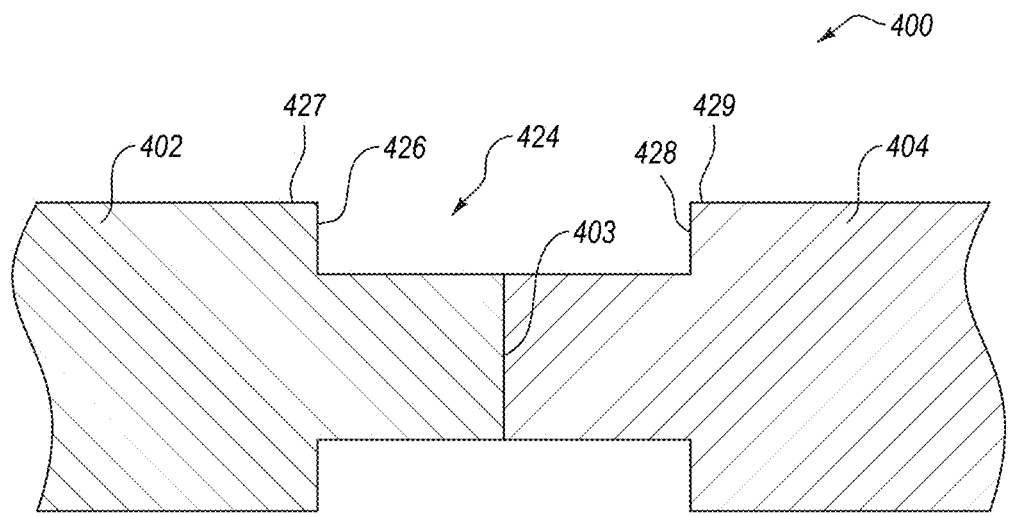
FIG. 5A is a side elevation and cross-sectional view showing the two welded segments of FIG. 4 once the weld region has been ground down and the weld nugget removed, before placement of the stiffness adjusting sleeve.

Referring to FIG. 5A, once the two segments have been joined together, the weld nugget 422 disposed therebetween can be removed, e.g., by grinding. For example, the weld nugget material extending laterally beyond the diameter of the adjacent proximal and distal segments may be ground away in a centerless grinding operation. As shown in FIG. 5A, the reduced diameter portion 424 may resemble a trough or pocket (used interchangeably herein) bounded by larger diameter sides or edges 426 of core wire portion 402 on the proximal side, and a larger diameter side or edge 428 of core wire portion 404 on the distal side. In other words, the reduction 424 surrounding weld joint 403 is to a smaller diameter than the final dimension of the metal core of guide wire 400 at location 424. As shown in comparison to FIG. 4, the lateral width of material removed may be greater than the thickness of weld nugget 422, and greater than the associated heat affected zone. For example, for a nominal guide wire diameter of 0.018 inch, and an actual wire diameter of 0.0165 inch to 0.0175 inch (the distal portion may be diametrically larger) at the weld joint, the thickness of material removed may be such that the reduced diameter over the weld joint 403 is from 0.004 inch to 0.0145 inch. The actual amount of reduction may depend on the location of the weld joint relative to the distal tip of the guide wire, e.g., a more distally disposed weld joint may be positioned within a portion of the core wire that is already reduced to a diameter that is less than the 0.0165 inch or 0.0175 inch starting diameter. In an embodiment, percentage reduction in diameter at the reduced trough 424 may be 5% to 75%, 8% to 55%, 10% to 50%, 10% to 20%, 10% to 25%, or 30% to 50% relative to the diameter at either the proximal side or distal side (e.g., 427 or 429, respectively). Examples showing various weld joint locations, nominal wire diameters, reduced wire diameters, and "top of the trough" wire diameters are shown below in Table 1. As will be apparent from Table 1, the percent reduction in diameter may depend on the weld joint location, with greater reductions being more typical where the weld joint is relatively closer to the distal tip. This characteristic is apparent when considered in light of, for practical reasons, the sleeve may typically have a wall thickness of about 0.001 inch to about 0.002 inch.

TABLE 1

| Weld Joint Location (Distance from Tip) | Nominal Wire Diameter | Wire Diameter (At bottom of trough) | Wire Diameter (At top of trough) | Percent Reduction in Diameter |
|---|---|---|---|---|
| 3 cm from tip | 0.018 inch | 0.004 inch | 0.006-0.008 inch | 33%-50% |
| 6 cm from tip | 0.018 inch | 0.0125 inch | 0.0145-0.0165 inch | 14%-24% |
| 10 cm from tip | 0.018 inch | 0.0145 inch | 0.0165-0.0175 inch | 12%-17% |
| 25 cm from tip | 0.018 inch | 0.0145 inch | 0.0165-0.0175 inch | 12%-17% |

As described herein, the weld joint 403 (and the stiffness adjusting sleeve 405) may be provided relatively close to the distal end (i.e., the distal tip) of the guide wire 400. This can present a particularly difficult problem where the weld joint may be significantly more likely to encounter tight curvature as the guide wire is advanced through the vasculature or other body lumen. For example, in an embodiment, the weld joint may be disposed no more than 25 cm from the distal end, no more than 20 cm from the distal end, no more than 15 cm from the distal end, or no more than 10 cm from the distal end. For example, the weld joint may be from about 3 cm to 25 cm (e.g., 3 cm from the distal end, 6 cm from the distal end, 10 cm from the distal end, 15 cm from the distal end, 20 cm from the distal end, or 25 cm) from the distal end.

Figure 5B:
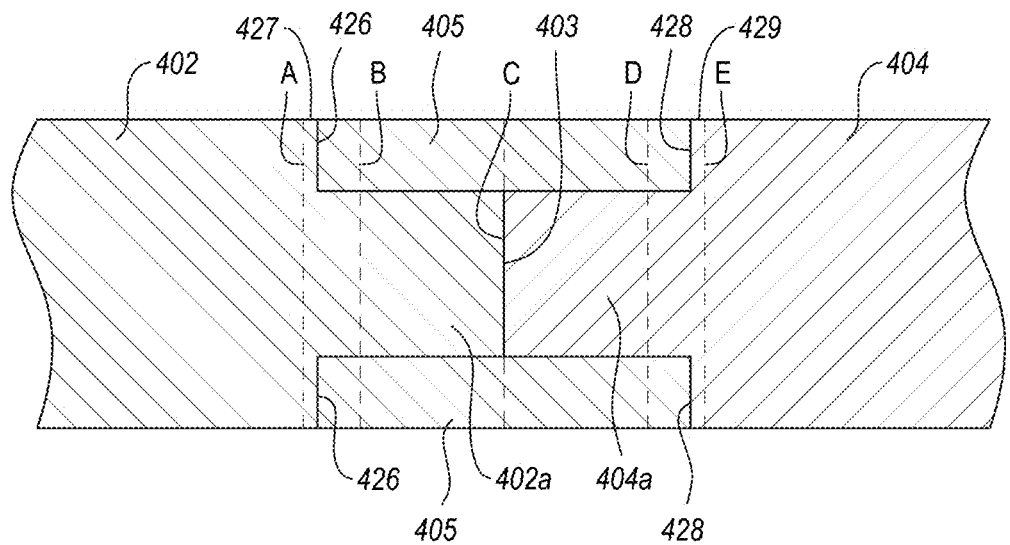
FIG. 5B is a side elevation and cross-sectional view similar to that of FIG. 5A once the sleeve has been positioned over the weld joint.

As shown in FIG. 5B, once the reduction in diameter surrounding the weld joint is achieved, the stiffness adjusting sleeve 405 may be positioned and affixed across dissimilar weld joint 403, within trough 424. Such a stiffness adjusting sleeve 405 may be hollow and generally cylindrical. Sleeve 405 may be positioned over trough 424 using any suitable technique. For example, in an embodiment, the hollow sleeve may be provided with an inside diameter that is initially greater than that of the distal and/or proximal core wire portions. The sleeve may be advanced from one end over the appropriate portion, so as to be over the trough 424. Once positioned over pocket or trough 424 the sleeve may be reduced in diameter through any suitable process, e.g., rotary swaging, crimping, and/or drawing, etc.

In an embodiment a longitudinal slit may initially be provided within sleeve 405 (e.g., along its full length), allowing its expansion over trough 424, followed by subsequent contraction of the sleeve 405 over the trough (e.g., through rotary swaging, crimping, drawing, etc. to fix sleeve 405 relative to trough 424. Where a longitudinal slit is provided, and where the material of sleeve 405 is sufficiently flexible, it may be possible to expand an opening through the slit by simply pressing or otherwise advancing sleeve 405 transversely, directly over the trough 424, without having to axially advance it over an end of the guide wire. For example, it may be possible to stretch or pull a nitinol sleeve open at such a slit, and press the sleeve over the trough. Once positioned over the trough 424, the sleeve may snap back to its original configuration. In such an embodiment, the sleeve may not have an inside diameter (before stretching) that is larger than that of the core wire portions.

Of course, advancement over an end of the guide wire may also be employed with a sleeve having a longitudinal slit, as desired. In any case, once the sleeve 405 is seated within reduced diameter trough 424, solder, braze, and/or an adhesive (e.g., glue) may be employed to aid in fixing sleeve 405 in position. The presence of sides 426 and 428 may aid in fixing sleeve 405, even if no solder, braze, or adhesive is used. Application of a polymer jacket over sleeve 405 at a subsequent step in the manufacturing process may further aid in fixing sleeve 405 in the desired position over reduced portion 424 and weld joint 403.

Sleeve 405 is advantageously configured (e.g., thickness, size, materials, etc.) to exhibit significant stiffness. The purpose of sleeve 405 is not merely to cover or reinforce weld joint 403, e.g., preventing unwanted separation of the welded core wire portions 402 and 404 (as sufficient strength is provided by the weld joint 403 alone). Rather, the purpose of sleeve 405 is to contribute significantly to the stiffness characteristics of the composite structure including the sleeve and underlying core wire portions 402 and 404, so as to create a more gradual change in stiffness, rather than an abrupt "stair step" as occurs with a weld joint alone. In other words, the stiffness value for the composite structure from any point between edge 426 and edge 428 is additive, and depends on the sum of the contributions from the thickness of the sleeve and the thickness of the reduced core portion 402a or 404a, depending on the latitudinal location through the composite structure. The contribution of the sleeve 405 for any given location will typically not be negligent. For example, at latitudinal location B, the overall stiffness characteristics of the composite structure are contributed by the thickness and material characteristics, etc. of sleeve 505 at location B in combination with the thickness and material characteristics, etc. of reduced in diameter core wire portion 402a (e.g., formed of stainless steel). At latitudinal location D, on the other side of weld joint 403, the stiffness characteristics of the composite structure are contributed by the thickness, material characteristics, etc. of sleeve 405 at location D in combination with the thickness, material characteristics, etc. of reduced core wire portion 404a (e.g., formed of nitinol). As described above, portion 404 (and 404a) may typically be formed from a material (e.g., nitinol, etc.) having significantly lower Young's modulus than the proximal portion 402 (e.g., stainless steel and/or a cobalt-based alloy, etc.).

Figure 9:
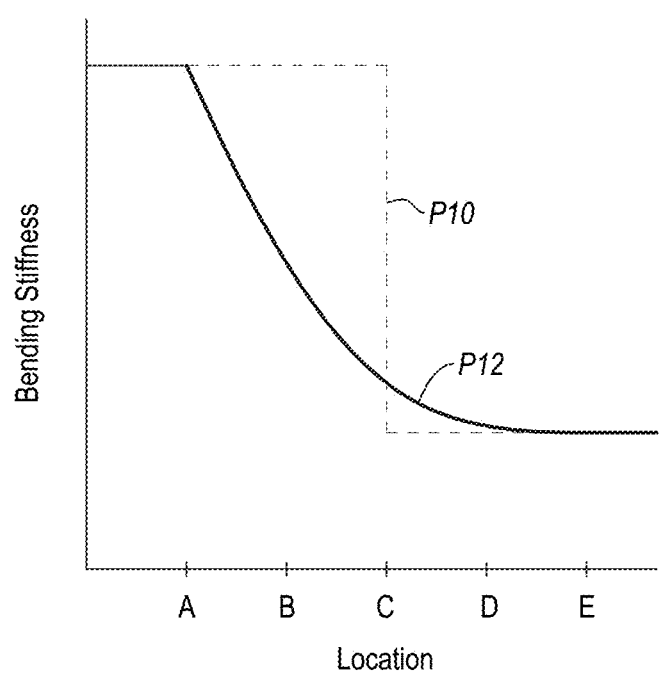
FIG. 9 plots an illustrative transition profile for bending stiffness across the proximal and distal core wire segments, comparing bending stiffness transition profiles with and without a stiffness adjusting sleeve positioned over the weld joint.

A transition profile such as would result by simply removing the weld nugget of FIG. 4, would result in a single abrupt change in stiffness, entirely at the weld joint 403. An embodiment as shown in FIG. 5B advantageously divides the magnitude of the change over a plurality of smaller "stair step" or even ramped changes (depending on the configuration of sleeve 405), and spreads this change over the length of the sleeve 405, resulting in a more gradual, less abrupt transition profile. An exemplary generalized plot is shown in FIG. 9, illustrating how the transition profile may be altered so as to no longer be so abrupt, but may be significantly more gradual. Line P10 plots an exemplary profile P10, showing a single stair-stepped change in bending stiffness, entirely at weld joint 403 (where no sleeve is used). Line P12 shows how the magnitude of the change in bending stiffness may be spread out over the length of the sleeve 405, with the change divided into multiple stair steps and/or gradual ramped changes.

Figure 9A:
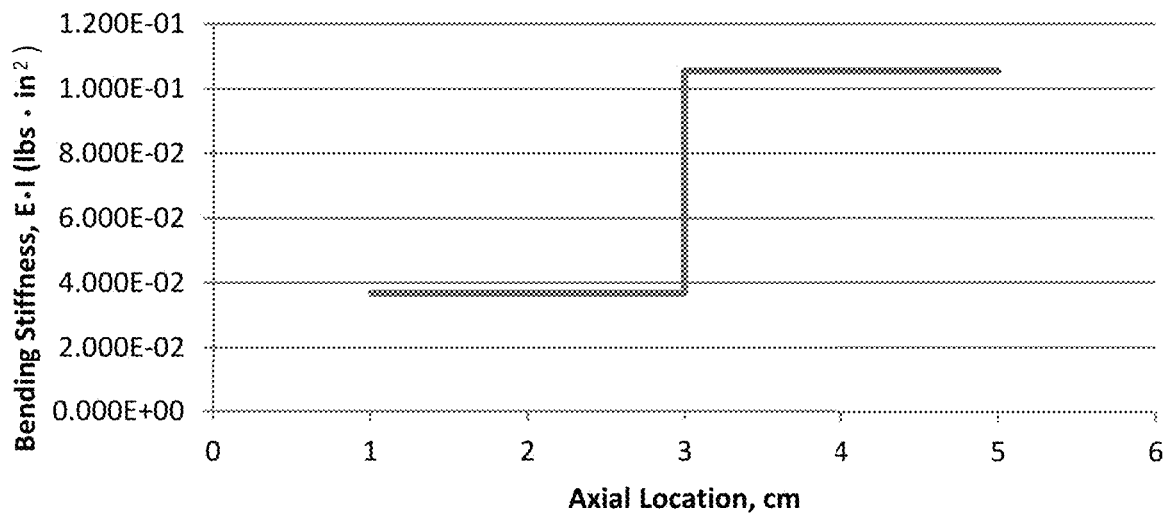
FIG. 9A plots an exemplary transition profile for bending stiffness across the proximal and distal core wire segments without any stiffness adjusting sleeve.
Figure 9B:
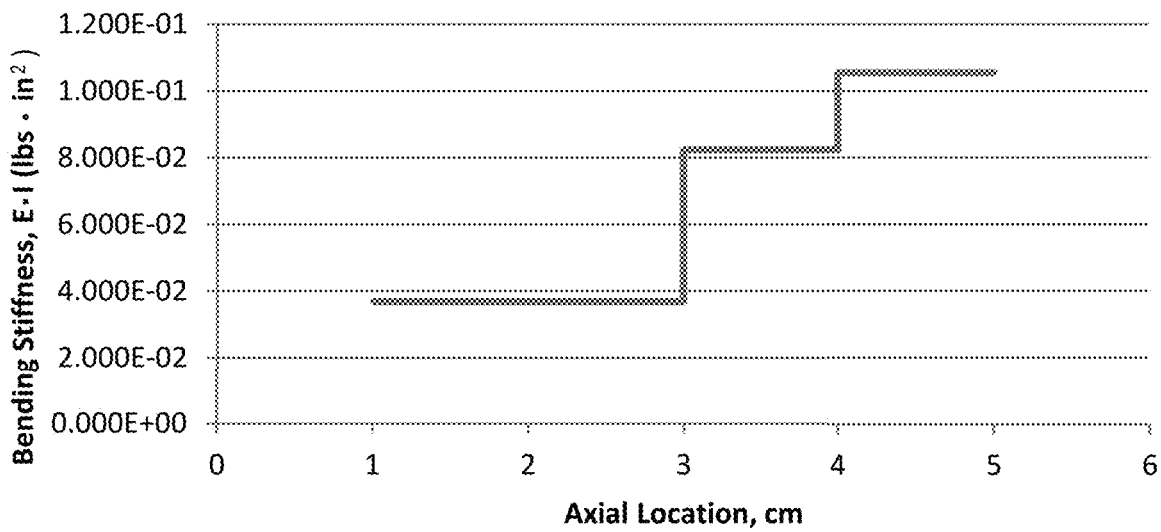
FIG. 9B plots an exemplary transition profile for bending stiffness across the proximal and distal core wire segments with a nitinol stiffness adjusting sleeve over the weld joint.
Figure 9C:
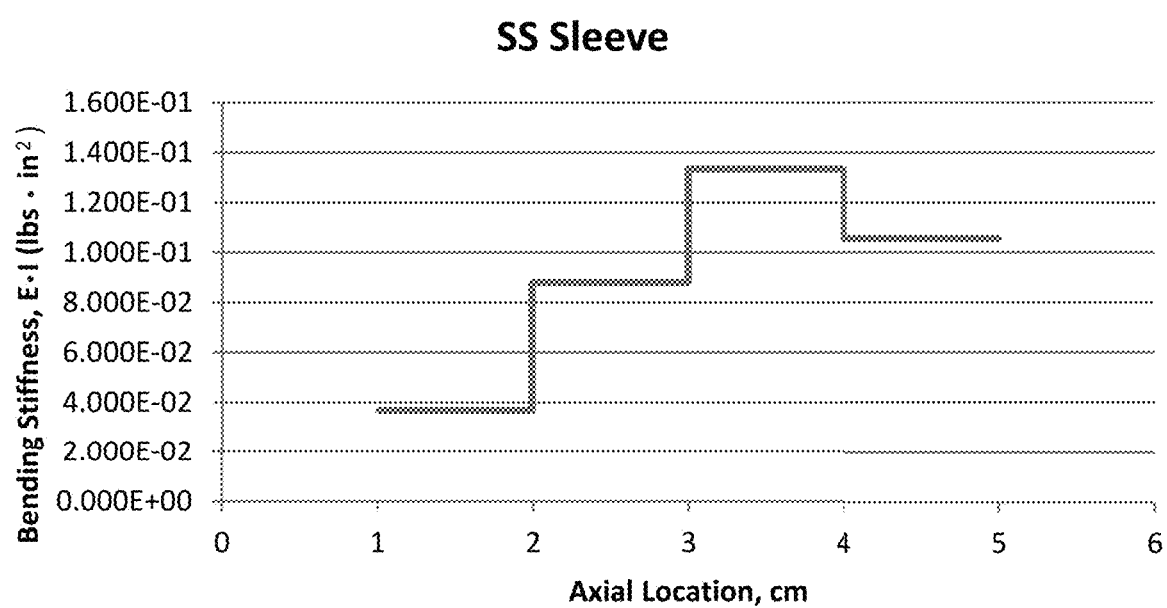
FIG. 9C plots an exemplary transition profile for bending stiffness across the proximal and distal core wire segments with a stainless steel stiffness adjusting sleeve over the weld joint.

FIGS. 9A-9C illustrate exemplary plots for bending stiffness for actual multi-segment guide wires including various sleeve configurations. The plot seen in FIG. 9A is for a configuration without any sleeve, based on a nitinol distal portion outside diameter of 0.0175 inch, which changes abruptly to a stainless steel proximal portion outside diameter of 0.0165 inch. The plot of FIG. 9B is for a configuration based on similarly sized guide wire portions, but with a nitinol sleeve disposed over the weld joint. The plot of FIG. 9C is for a configuration based on similarly sized guide wire portions, but with a stainless steel sleeve disposed over the weld joint. The specific sleeve and guide wire portion characteristics are as shown in the tables of FIGS. 10A-10C, with FIG. 10A corresponding to FIG. 9A, FIG. 10B corresponding to FIG. 9B, and FIG. 10C corresponding to FIG. 9C. In each example, the weld joint is at 3 cm (e.g., 3 cm from the tip), and the sleeve is 2 cm in length, centered over the weld joint. It will be apparent that any tapering and/or slots in the sleeve would alter the profile (e.g., making it even more gradual) further. Where 2 values are calculated for a given position (e.g., at 2 cm), those positions are immediately to either side of the stated location. For example, the 2 cm "Distal NiTi" is for the location at 2 cm that is through the nitinol distal guide wire portion. The 2 cm "Distal Sleeve" is for the location at 2 cm that is at the edge of the sleeve, through the distal end of the sleeve and the nitinol distal guide wire portion. The dual reported locations for 3 cm and 4 cm are similarly reported immediately on either side of the interface (e.g., weld interface or sleeve edge, respectively).

For each of the calculations in FIGS. 10A-10C, moment of inertia (I) for a solid cylinder of diameter D is calculated as $I=(Pi/64) \cdot D^4$. Moment of inertia of a solid cylinder of outer diameter D and inner diameter d is calculated as $I=[(Pi/64) \cdot D^4]-[(Pi/64) \cdot d^4]$. Bending stiffness (in $lbs_f \cdot in^2$) is calculated as I times modulus of elasticity (E).

Figure 6A:
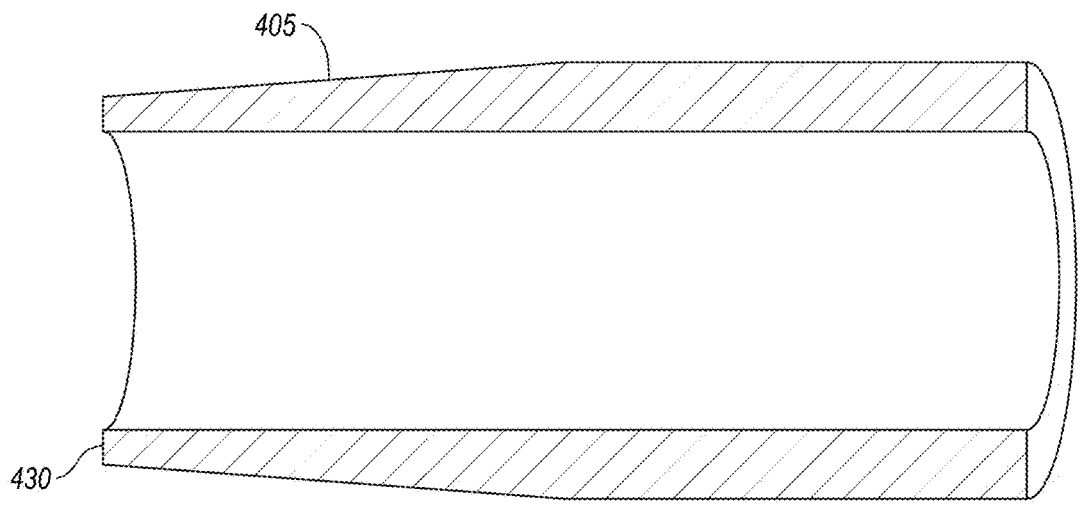
FIG. 6A shows a side elevation and partial cross-sectional view through an exemplary stiffness adjusting sleeve that is tapered in thickness at the proximal end of the sleeve.
Figure 6B:
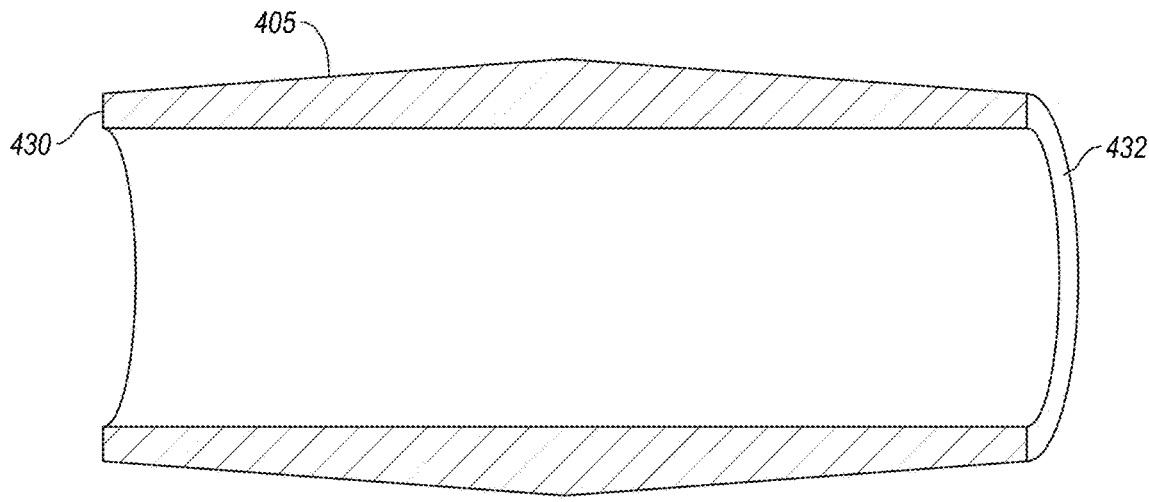
FIG. 6B shows a side elevation and partial cross-sectional view of a stiffness adjusting sleeve that is tapered in thickness at both the proximal and distal ends of the sleeve.

In order to further smooth the gradual change in bending stiffness across the transition of the guide wire, one or more specific features may be present within the stiffness adjusting sleeve. Examples of such features are shown in FIGS. 6A-6C, and FIG. 7. In an embodiment, the stiffness adjusting sleeve 405 may be formed from the same material as the distal core wire portion 404 (e.g., nitinol). As shown in FIGS. 6A-6B, one or both ends of sleeve 405 may be tapered (e.g., taper ground) to gradually change its bending stiffness. In other words, in addition to the selection of the material from which sleeve 405 is formed, its thickness also affects how much stiffness it adds at any given latitudinal location along the transition covered by sleeve 405. As shown in FIG. 6A, in an embodiment, only the proximal end 430, is tapered. This is advantageous as it is the proximal end 430 which abuts the stainless steel edge 426, positioning the tapered portion over the stainless steel reduced portion 402a. In an embodiment, the taper may extend over the proximal half of sleeve 405, so that the taper ends at location C (FIG. 5B) over the weld joint 403. In this manner, no taper may be present over the reduced diameter nitinol portion 404a. This is advantageous as the stainless steel material already exhibits greater bending stiffness than the nitinol. Thus, the sleeve and reduction in diameter across portion 424 thus serves to reduce the bending stiffness from the start of the sleeve, to location C (the weld joint) relative to what it would have been with no sleeve and no diameter reduction.

As shown in FIG. 6B, in another embodiment, both ends 430 and 432 of sleeve 405 may be tapered. The embodiment of FIG. 6A may be preferred, as there may be no benefit in reducing stiffness (through tapering) on the nitinol side of the weld joint, as this already represents the portion exhibiting the lowest bending stiffness, and it may be desired to raise stiffness on this end, rather than decrease stiffness. In effect, the embodiment of FIG. 6A may serve to gradually bring the bending stiffness of the stainless steel side of the core wire down towards the bending stiffness of the nitinol side, a smoothly (i.e., not stair-stepped) gradual decrease in bending stiffness being provided at least over the tapered proximal portion of sleeve 405.

Figure 6C:
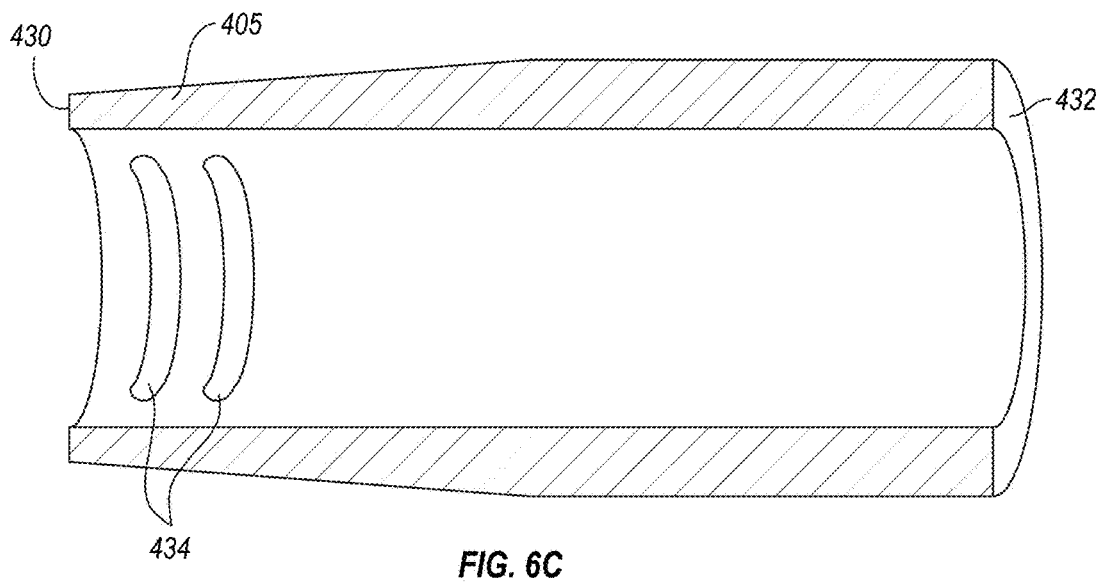
FIG. 6C shows a side elevation and partial cross-sectional view of a stiffness adjusting sleeve including slots formed in the proximal end of the sleeve.
Figure 8:
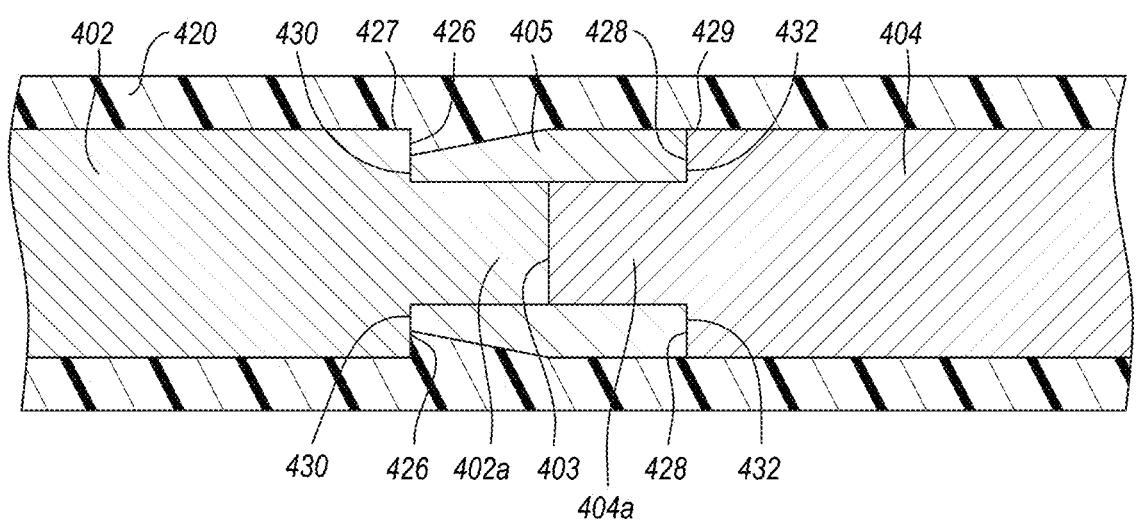
FIG. 8 shows a cross-sectional view of a weld region including a stiffness adjusting sleeve similar to that of FIG. 6A disposed over the weld region, with both sides of the weld region having been reduced in diameter to accommodate the sleeve, and a polymer jacket disposed over the weld region.

Another mechanism for reducing stair-stepped changes (or at least the magnitude thereof) in the bending stiffness transition profile is to provide slots (e.g., a pattern of slots) into the sleeve 405. As shown in FIG. 6C, such slots 434 may be formed into the proximal portion of sleeve 405, so that slots 434 are disposed over the stainless steel portion 402a. In a similar manner as the tapering of FIG. 6A, slots 434 further serve to reduce bending stiffness within the proximal transition portion (i.e., the proximal half of sleeve 405 that is disposed over stainless steel portion 402a). Relatively higher density patterning of the slots 434 serves to further reduce stiffness (i.e., higher density of slots results in relatively lower stiffness). The slot density may vary across the sleeve 405 (e.g., highest density adjacent the proximal end 430). While FIG. 6C shows slots 434 in combination with tapering along the proximal half towards proximal end 430, it will be appreciated that in another embodiment, no tapering may be provided with the slots 434. In another embodiment, slots may be provided within either or both of the proximal or distal halves of sleeve 405. Tapering of either or both halves may be provided as described herein.

Where tapering or slots are provided, any difference in outside dimension (e.g., diameter) as a result of such features may be covered or filled with the polymer jacket which may be applied subsequently during manufacture. For example, as will be apparent from FIGS. 6A and 5B, if the tapered sleeve 405 of FIG. 6A were placed in trough 424 of FIG. 5B (replacing the sleeve of FIG. 5B, which is shown as untapered), a gap may be present where edge 426 may not be fully covered by proximal end 430 of sleeve 405 of FIG. 6A, as it may have insufficient height to do so. Such a gap may be filled when applying a polymer jacket over the core wire portions 404, 402 and sleeve 405. FIG. 8 shows such an example, illustrating how gap 429 that may result where a proximal taper is provided, may be filled by polymer jacket 420. It will be appreciated that where the sleeve includes one or more slots formed therein, the slots may similarly be filled with the polymer jacket during manufacture. Such a polymer jacket may be applied through any suitable process, e.g., through extrusion, coextrusion, gap-filling polymeric adhesives, etc. Examples of polymer jacketed guide wires are disclosed in U.S. Pat. Nos. 6,673,025; 7,455,646; and 7,494,474, each of which is herein incorporated by reference. Such a polymer jacket may aid in preventing occurrence of an inner-lumen collapse event, e.g., where a balloon may collapse and lock onto a bare wire. Such a polymer jacket may be relatively lubricious, providing a low friction surface (e.g., coated with PTFE, hydrophilic polymer, or similar).

Figure 7:
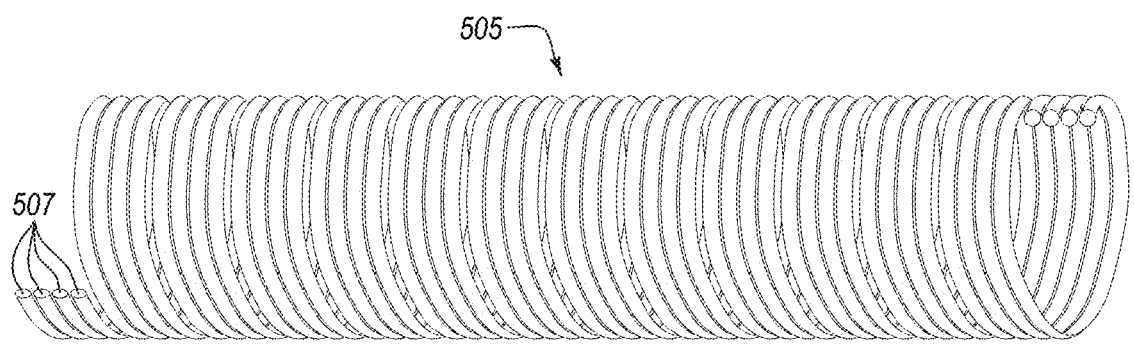
FIG. 7 shows a perspective view of a stiffness adjusting sleeve that is formed from a multifilar coil including multiple strands of helically wound wire.

FIG. 7 shows another mechanism for providing a stiffness adjusting sleeve 505. In the embodiment of FIG. 7, the stiffness adjusting sleeve 405 is configured as a multifilar coil, e.g., including multiple strands 507 of helically wound metallic wire. Although illustrated with four separate strands 507, it will be appreciated that more or fewer strands may similarly be employed (e.g., 2, 3, 4, 5, 6, etc.). Such a multifilar coil construction is inherently more flexible as compared to tubing including similar dimensions (e.g., same inner and outer diameter). The lay angle of the individual strands may be about 45° relative to the coil longitudinal axis, but can easily be varied by altering the strand count and/or strand diameter. Such a multifilar structure is also less apt to act as a spring (and more like a tube), than a monofilar coil. Such a multifilar coil exhibits greater stiffness than a similarly dimensioned monofilar coil, yet is very flexible. Such multifilar coils may include similar dimensions as the other sleeves herein (e.g., a difference between inner and outer diameter typically from 0.002 to 0.004 inch, and a length typically from 0.75 cm to 1.5 cm, or any of the values described herein for the sleeve). As will be apparent, if it is desired to include slot patterning within the stiffness adjusting sleeve, a tube construction may be preferred over multifilar coil, although tapering (e.g., taper grinding) may be possible with a multifilar coil where care is taken to ensure fraying is minimized or prevented. For example, when employing a multifilar coil any cutting or tapering may be achieved through laser cutting or similar process, as the ends of the individual strands may tend to fuse or otherwise adhere together (much like the melting of the end of a nylon rope) during such procedure. A similar fusing may be achieved through laser welding of the ends of the multifilar strands 507 to one another and/or to adjacent core wire portions 402 or 404 (e.g., sidewall edges 426 and 428). In an embodiment, an end of the multifilar coil could be dipped or otherwise include solder thereon, and then be cut (either laser cut or otherwise). Any fraying ends may become embedded in the solder, holding them in place to prevent further fraying. Such "pretining" of the ends with solder or similar material and then cutting (e.g., laser, mechanical, electro-discharge machining "EDM", etc.) may minimize or prevent fraying.

Even without any laser welding or laser cutting of a multifilar coil, any tendency for the ends of a multifilar coil sleeve to fray may be minimized or prevented where the entire transition portion comprising the sleeve, typically some portion of the adjacent proximal core wire portion (and typically the entire distal core wire portion) are encased within the polymer jacket. Such a polymer jacket may thus serve to trap any stray ends of a multifilar coil sleeve. Any of the other features described with respect to any of the other stiffness adjusting sleeves may likewise be employed within a multifilar stiffness adjusting sleeve.

In any case, any of the various contemplated stiffness adjusting sleeves in combination with the reduced diameter surrounding weld zone 403 serves to reduce the abruptness of the change in bending stiffness across a dissimilar metal weld joint where the two metals differ significantly in their Young's modulus values. The change in stiffness across the core wire is reduced by grinding or otherwise reducing the weld region for some distance on either side of the weld joint 403 to a smaller diameter (e.g., smaller than the final outside diameter of the adjacent metallic guide wire core locations 427 and 429 of FIG. 5A). The transition is further less abrupt by virtue of the stiffness adjusting sleeve, which spreads the transition over a greater length as compared to where no such sleeve is provided, where the entire transition occurs exactly at the weld joint where both core wire portions meet.

As described herein, in order to bring the bending stiffness values of the proximal and distal core wire portions closer to one another, the proximal metallic core wire portion 402 may be formed so as to have a smaller outside diameter than the distal metallic core wire portion 404. The larger diameter of the distal metallic core wire portion (which is formed of a material having a lower Young's modulus than the proximal metallic core wire portion) at least partially compensates for the lower Young's modulus, increasing its bending stiffness to be closer to that of the proximal core wire portion. For example, for a nominal 0.018 inch guide wire, the proximal core wire portion 402 may have a diameter of 0.0165 inch, and the distal core wire portion 404 may have a diameter of 0.0175 inch. A polymer jacket may cover at least the weld joint, any sleeve, and/or at least a part of the distal core portion. For example, the distal core wire portion 404 may have a diameter than is 2% to 15%, 3% to 10%, or 4% to 8% (e.g., 6%) larger than that of the proximal core wire portion 402.

Any such differences in the outside diameter of the metallic core wire portions 402 and 404 may be filled in when applying a polymer jacket over the sleeve and the weld joint. For example, such a polymer jacket (see FIGS. 3 and 8) may encase the distal end of the guide wire, up to and including the stiffness adjusting sleeve, so that the polymer jacket coating presents a constant overall diameter (or at least a smooth exterior surface—which could be tapered) to the guide wire. In an embodiment, the exterior profile across at least the sleeve and the weld region may be constant in diameter, or include otherwise desirable dimensional uniformity (e.g., smooth—typically constant exterior diameter, but tapering possible). In embodiments where the sleeve is positioned over a tapered portion of the guide wire metallic core, the taper may continue under the polymer jacket, within the sleeve and metallic core wire of the guide wire. Any effect of the polymer jacket on bending stiffness may be insignificant as compared to the effect of the metallic core wire portions and sleeve (e.g., less than 10%, less than 5%, less than 3%, less than 2%, less than 1% of the total contributions to bending stiffness).

Any of the features described herein in the context of a particular embodiment may be employed within any other of the embodiments described herein.

Numbers, percentages, or other values stated herein are intended to include that value, and also other values that are about or approximately the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing process, and may include values that are within 10%, within 5%, within 1%, etc. of a stated value. Furthermore, the terms "substantially", "about" or "approximately" as used herein represents an amount close to the stated amount that still performs a desired function or achieves a desired result. For example, the term "substantially" "about" or "approximately" may refer to an amount that is within 10% of, within 5% of, or within 1% of, a stated amount or value.

It must be noted that, as used in this specification and the appended claims, the singular forms "a," "an" and "the" include plural referents unless the context clearly dictates otherwise.

All publications, patents and patent applications cited herein are hereby incorporated by reference in their entirety to the same extent as if each individual publication, patent or patent application was specifically and individually indicated to be incorporated by reference.

The embodiments of the present disclosure may be embodied in other specific forms without departing from its spirit or essential characteristics. The described embodiments are to be considered in all respects only as illustrative and not restrictive. Therefore, the scope of the disclosure is indicated by the appended claims rather than by the foregoing description. All changes that come within the meaning and range of equivalency of the claims are to be embraced within their scope.

The invention claimed is:

1. A method for forming a multi-segment intraluminal guide wire, the method comprising:
   providing initially separate distal and proximal guide wire segments, which segments comprise different metallic materials;
   aligning the separate distal and proximal segments end-to-end;
   welding the distal segment directly to the proximal segment at a weld joint;
   reducing a diameter of a weld region surrounding the weld joint relative to a diameter of the distal and proximal segments of the guide wire on either side of the weld region;
   positioning a stiffness adjusting sleeve over the weld region, the stiffness adjusting sleeve being formed from:
      a multifilar coil including multiple strands of helically wound wire disposable over the weld region so that a transition profile of bending stiffness across the weld region is gradual rather than abrupt across a distal portion of the guide wire to a proximal portion of the guide wire; or
      a sleeve body in which at least one end thereof is tapered in thickness so that a transition profile of bending stiffness across the weld region is gradual rather than abrupt across the distal portion of the guide wire to the proximal portion of the guide wire.

2. The method of claim 1, further comprising covering at least the sleeve and the weld region with a polymer jacket so that an exterior surface of the guide wire presents a constant overall diameter profile across at least the sleeve and the weld region.

3. The method of claim 1, further comprising providing a diameter to the proximal segment that is less than a diameter of the distal segment to aid in reducing any difference in bending stiffness between the proximal and distal segments of the guide wire.

4. The method of claim 1, wherein the distal segment comprises nitinol and the proximal segment comprises at least one of stainless steel or a cobalt-based alloy.

5. The method of claim 1, wherein the weld joint is disposed from about 3 cm to 25 cm from a distal end of the distal portion.

6. The method of claim 1, wherein ends of the distal and proximal segments are generally perpendicular to a longitudinal axis of the segments, so that the resulting weld joint is generally perpendicular to the longitudinal axis of the resulting guide wire.

7. A method for forming a multi-segment intraluminal guide wire, the method comprising:
providing initially separate distal and proximal guide wire segments, which segments comprise different metallic materials;
aligning the separate distal and proximal segments end-to-end;
welding the distal segment directly to the proximal segment at a weld joint;
following welding the distal segment and the proximal segment, reducing a diameter of a weld region surrounding the weld joint relative to a diameter of the distal and proximal segments of the guide wire on either side of the weld region;
positioning a stiffness adjusting sleeve over the weld region, the stiffness adjusting sleeve forming a transition profile of bending stiffness across the weld region to be gradual rather than abrupt across a distal portion of the guide wire to a proximal portion of the guide wire,
wherein, the stiffness adjusting sleeve comprises:
a multifilar coil including multiple strands of helically wound wire disposable over the weld region; or
a sleeve body in which at least one end thereof is tapered in thickness.

8. The method of claim 7, further comprising covering at least the sleeve and the weld region with a polymer jacket so that an exterior surface of the guide wire presents a constant overall diameter profile across at least the sleeve and the weld region.

9. The method of claim 7, wherein ends of individual strands of the multifilar coil are adhered to one another to prevent them from fraying.

10. The method of claim 7, wherein both ends of the sleeve body are tapered.

11. The method of claim 7, further comprising providing a diameter to the proximal segment that is less than a diameter of the distal segment to aid in reducing any difference in bending stiffness between the proximal and distal segments of the guide wire.

12. The method of claim 7, wherein the weld joint is disposed from about 3 cm to 25 cm from a distal end of the distal portion.

13. The method of claim 7, wherein the weld joint is disposed no more than 25 cm from a distal end of the distal portion.

14. The method of claim 7, wherein the weld joint is disposed no more than 20 cm from a distal end of the distal portion.

15. The method of claim 7, wherein the weld joint is disposed no more than 15 cm from a distal end of the distal portion.

16. The method of claim 7, wherein the weld joint is disposed no more than 10 cm from a distal end of the distal portion.

17. The method of claim 7, wherein ends of the distal and proximal segments are generally perpendicular to a longitudinal axis of the segments, so that the resulting weld joint is generally perpendicular to the longitudinal axis of the resulting guide wire.

18. A method for forming a multi-segment member, the method comprising:
aligning separate distal and proximal segments end-to-end, the distal and proximal segments comprising different metallic materials with different Young's modulus;
welding the distal segment to the proximal segment at a weld joint;
reducing a diameter of a weld region surrounding the weld joint relative to a diameter of the distal and proximal segments of the multi-segment member on either side of the weld region to form a reduced diameter portion;
positioning a stiffness adjusting sleeve over the weld region and within the reduced diameter portion, the stiffness adjusting sleeve forming a transition profile of bending stiffness across the weld region to be gradual rather than abrupt across a distal portion of the guide wire to a proximal portion of the guide wire, the stiffness adjusting sleeve comprising a tapered outer surface having a diameter less than a diameter of the distal and proximal segments of the guide wire on either side of the reduced diameter portion.

19. The method of claim 18, wherein the stiffness adjusting sleeve comprises:
a multifilar coil including multiple strands of helically wound wire disposable over the weld region; or
a sleeve body in which at least one end thereof is tapered in thickness.

* * * * *